United States Patent [19]

Benazzi et al.

[11] Patent Number: 5,523,506
[45] Date of Patent: Jun. 4, 1996

[54] CATALYST WITH AN OMEGA ZEOLITE BASE, CONTAINING AT LEAST ONE GROUP IIA, IVB, IIB OR IVA METAL, AND USE THEREOF IN THE ISOMERIZATION OF AN AROMATIC C8 CUT

[75] Inventors: Eric Benazzi, La Celle St. Cloud; Jean-Francois Joly, Paris; Christine Travers, Rueil Malmaison; Jean-Marie Basset; Agnes Choplin, both Villeurbane, all of France

[73] Assignee: Institut Francais Du Petrole, Rueil Malmaison, France

[21] Appl. No.: 294,709

[22] Filed: Aug. 23, 1994

Related U.S. Application Data

[62] Division of Ser. No. 57,379, May 6, 1993, Pat. No. 5,391,528.

[30] Foreign Application Priority Data

May 6, 1992 [FR] France ................................ 92 05680

[51] Int. Cl.[6] ...................................................... C07C 5/27
[52] U.S. Cl. ............................ 585/481; 585/480; 585/482
[58] Field of Search ..................................... 585/480, 481, 585/482

[56] References Cited

U.S. PATENT DOCUMENTS

| | | |
|---|---|---|
| 3,013,987 | 12/1961 | Castor et al. . |
| 3,691,101 | 9/1972 | Mertzweiller et al. . |
| 3,783,123 | 1/1974 | Young . |
| 4,724,067 | 2/1988 | Raatz et al. . |
| 5,391,528 | 2/1995 | Benazzi et al. ............................ 502/66 |

FOREIGN PATENT DOCUMENTS

| | | |
|---|---|---|
| 7126 | 1/1980 | European Pat. Off. . |
| 206871 | 12/1986 | European Pat. Off. . |
| 210991 | 4/1989 | European Pat. Off. . |
| 329305 | 8/1989 | European Pat. Off. . |
| 458674 | 11/1991 | European Pat. Off. . |
| 1117568 | 6/1968 | United Kingdom . |

*Primary Examiner*—Asok Pal
*Attorney, Agent, or Firm*—Millen, White, Zelano & Branigan

[57] ABSTRACT

The invention relates to an alumino-silicate type catalyst containing an omega zeolite with a Si/Al atomic ratio of between 2.5 and 100, with a content by weight of sodium of less than 2000 ppm (in relation to the weight of dry zeolite) and further containing, at least one metal selected from group IIa, IIb, and IVa metals, and at least one group VIII metal.

The catalyst is prepared by the grafting of an organometallic compound of said group IIa, IVb, IIb, IVa metals.

The catalyst is particularly suitable for the isomerization of an aromatic $C_8$ cut.

11 Claims, No Drawings

:5,523,506

CATALYST WITH AN OMEGA ZEOLITE BASE, CONTAINING AT LEAST ONE GROUP IIA, IVB, IIB OR IVA METAL, AND USE THEREOF IN THE ISOMERIZATION OF AN AROMATIC C8 CUT

This application is a divisional of application Ser. No. 08/057,379, filed May 6, 1993, now U.S. Pat. No. 5,391,528.

SUMMARY OF THE INVENTION

The present invention relates to an alumino-silicate type catalyst comprising an omega zeolite (of the MAZZITE structural kind), the geometrical selectivity and/or the catalytic properties of which has/have been modified by depositing on the outer surface of the crystals at least one metal selected from groups IIa (Be, Mg, Ca, Sr, Ba, Ra), group IVb (Ti, Zr, Hf), group IIb (Zn, Cd, Hg) and IVa (Ge, Sn, Pb) of the periodic classification of elements, possibly at least one group VIII metal of said classification and a matrix, and use thereof in reactions for the isomerization of aromatic $C_8$ hydrocarbons. The invention also relates to the process for the preparation of said modified omega zeolite.

At present, the catalysts used industrially in these reactions mainly have a ZSM-5 zeolite base, on its own or mixed with other zeolites such as mordenite, for example. These catalysts are described, in particular, in the patents U.S. Pat. No. 4,467,129 and in U.S. Pat. No. 4,482,773. The ZSM5 zeolite is worthwhile because it has excellent shape selectivity which results in large paraxylene selectivity as far as undesirable secondary dismutation reactions are concerned which remain at a very low level.

Other 12MR zeolites with larger pore openings (opening with 12 oxygen atoms) have also been used, such as mordenite and omega zeolite. The catalysts with a mordenite or an omega zeolite base are described, in particular, in the U.S. Pat. No. 4,723,051 and in U.S. Pat. No. 4,665,258. However, these zeolites do not have any special geometric selectivity properties. Irrespective of the Si/Al ratio, this means that the paraxylene selectivities are lower than those obtained for MFI zeolite, and also, in particular, that there is a very large production of trimethyl benzenes. The patent application WO90/09845 provides a solution which allows the dismutation rate of xylenes to be reduced, in instances where the catalysts are mordenite based catalysts, by the grafting of organometallic compounds on the mordenite. Omega zeolite is a very active zeolite in the isomerization reaction of $C_8$ aromatics. Nonetheless, the production of trimethylbenzenes by dismutation is actually greater in the omega zeolite than in ZSM5.

The invention relates to a catalyst containing a matrix, at least one group VIII metal and an omega zeolite wherein said omega zeolite includes at least one metal selected from group IIa, IVb, IIb and IVa group metals of the periodical classification of elements, and is such that its global Si/Al atomic ratio is between 2.5 and 100 and its content by weight of sodium in relation to the weight of dry omega zeolite is less than 2000 ppm, said group IIa, IIb, IVa, IVb group metal (or metals) being deposited on the omega zeolite by grafting with at least one organometallic compound of said metal(s).

The Applicant has in fact discovered that it is possible, by way of depositing on the outer surface of the omega zeolite crystals at least one metal selected from group IIa, IVb, IIb and IVa metals, in particular magnesium, titanium, zinc and/or tin, to obtain active catalysts which are selective for the isomerization reaction of $C_8$ aromatics. This new preparatory process imparts to the omega zeolite greatly improved geometric selectivity properties, which is revealed by a significant inhibition of undesirable secondary reactions such as dismutation. This new modified omega zeolite also results in selectivities in respect of parasitic desalkylation reactions which are less than those of catalysts with a ZSM5 base. Solids are therefore obtained which not only show better performance than prior art omega zeolites with respect to the isomerization of $C_8$ aromatics, but which are at least the same as, if not better, in performance than catalysts with a ZSM5 base.

Secondly, it has been surprisingly discovered that regeneration of the catalyst with an omega zeolite base, the outer surface of crystals of which has been subjected to a deposit of at least one metal selected from group IIa, IVb, IIb and IVa group metals permits improved activity to be obtained in this case.

Before selecting the porous network of the omega zeolite by the deposit of at least one group IIa, IVb, IIb, IVa group metal it is preferable to use the $H^+$ or $NH_4^+$ form of said omega zeolite with a content by weight of sodium in relation to the weight of dry omega zeolite which is usually less than 2000 ppm, preferably less than 1000 ppm, and still more preferably less than 500 ppm, an atomic Si/Al ratio of between 2.5 and 100, preferably between 3 and 25, an absorption capacity of nitrogen which is measured at −196° C. at partial pressure $P/P_o=0.19$, greater than 0.096 $cm^3$ liquid/gramme. The content by weight of water in the omega zeolite in $H^+$ or $NH_4^+$ form is usually between 5 and 50%.

To prepare said $H^+$ or $NH_4^+$ form it is possible to use any technique known in the art, such as direct acid attack, calcination in the presence or absence of water vapour in $NH_4^+$ form, followed by one or more acid attacks, "calcination—acid attack(s)" cycles.

Depositing at least one of the selected metals in the assembly formed by the group IIa, IVb, IIb and IVa metals is advantageously effected by grafting using as the grafting agent at least one organometallic compound of said metal which is firstly sufficient in bulk not to penetrate inside the microporous network of the omega zeolite and which is also capable of reacting with the OH surface groups. The grafting agents which can be used, in particular in the case of tin, are formula $SnR^1R^2R^3R^4$ compounds wherein the $R^1$, $R^2$, $R^3$ and $R^4$ groups which are identical or different are organic groups of varied bulk, which are usually of great bulk; as non-limitative examples it is possible to cite alkyl radicals, aryl, organosilyl vinyl, polynuclear aryl, cyclo-alkyl, allyl, propargyl. The $R^i$ groups, i=1,2,3 or 4 can also be a group of the alkoxy type or obstructed aryl-oxy type such as a ter-butoxy group, o,o'-diphenyl phenoxy group, o'-di-isopropyl phenoxy group etc.

The $R^i$ group can also be a hydride, but at least one organic $R^i$ group remains fixed to the tin, as non-limitative examples it is possible to cite the compounds $SnBu_2H_2$ and $SnBu_3H$ in the case of tin.

Usually, with the other group IIa metals (Be, Mg, Ca, Sr, Ba, Ra) and group IVb metals (Ti, Zr, Hf), group IIb metals (Zn, Cd, Hg) and group IVa metals (Ge, Sn, Pb) it is possible to use grafting agents in the form of compounds of formula $BeR_2$, $MgR_2$, $CaR_2$, $SrR_2$, $BaR_2$, $RaR_2$, $TiR_4$, $ZrR_4$, $HfR_4$, $CdR_2$, $GeR_4$, $SnR_4$ or $PbR_4$ wherein $R^i$ which may be identical to or different from each other are organic groups such as those defined hereinabove.

As non-limitative examples in the case of tin a grafting agent is preferred which is tetrabutyl tin $SnBu_4$. In the case of magnesium a grafting agent is preferred which is bisneopentyl magnesium $MgNp_2$, and in the case of zirconium a grafting agent is preferred which is tetraneopentyl zirconium $ZrNp_4$, and in the case of germanium a grafting agent is preferred which is tetrabutyl germanium $GeBu_4$.

The preparation stages for the grafted zeolite are as follows:

Pre-treatment of the omega zeolite

The zeolite is pre-treated by one of two methods described hereinafter:

Activation with inert gas flow ($N_2$, for example)

Usually, after being placed in inert gas at a temperature of between about 50° C. and 200°, preferably about 150° C., for 8 to 24 hours, for about 12 hours, for example, (drying stage), calcination is carried out of the omega zeolite at a temperature of between 410° C. and 580° C., preferably at about 550° C. for a period of time of between 1 and 8 hours, preferably about 4 hours, with gaseous mixture of inert gas and air. The temperature is then reduced with inert gas until a temperature of between 5° C. and 35° C., preferably about 20° C., is reached.

Pre-treatment under vacuum

The omega zeolite is heated to a temperature of between 120° C. and 200° C., preferably 160° C., for a length of time which is sufficient to obtain a vacuum of $133.10^{-4}$ Pa. The temperature is then increased to a value of between 400° and 500° C., preferably to about 450° C. The omega zeolite which is thus activated is cooled again under vacuum to a temperature of between 5° C. and 35° C., preferably to about 20° C., and is then kept in an inert atmosphere.

Grafting of the omega zeolite

At least one grafting agent can be fixed to the omega zeolite by a gaseous phase method or by an aqueous phase method. In this latter case, the organometallic compound selected is then placed in solution in a solvent, such as hexane, in inert gas.

By way of an illustrative and non-limitative example in the case of $SnBu_4$, one of the following procedures is used in the knowledge that similar methods are used with the other grafting agents cited hereinabove:

Grafting by gaseous phase method

The zeolite which has been pre-treated in the ways described hereinabove is placed in a static vacuum ($133.10^{-4}$ Pa) at 25° C., in a closed recipient. The organometallic compound, in this case $SnBu_4$, is injected at 25° C. by the intermediary of a septum.

The temperature at which the grafting is carried out is advantageously greater than about 50° C. for $SnBu_4$. For other compounds and as a non-limitative example a temperature of about 250° C. is used for $GeBu_4$, about 150° C. is used for $MgNp_2$, and about 80° C. is used for $ZrNp_4$.

The durations of the treatment are usually greater than 1 minute and are advantageously between 1 hour and 24 hours and preferably about 12 hours. After grafting, the excess $Bn(Bu)_4$ present in the system is usually eliminated by purging under dynamic vacuum or with inert gas.

Grafting by liquid phase method

The omega zeolite is placed in suspension in a solvent of the grafting agent constituted of at least one alkane with at least 5 carbon atoms, such as hexane, in inert gas. The volume V of hexane used (in ml) is between about once and 50 times the weight of dry omega zeolite used, that is to say a V/P of between 1 and 50, preferably about 3. The grafting agent, $SnBu_4$, for example, is then introduced. The temperature at which the zeolite is placed in contact with the grafting agent is advantageously higher than the congealing temperature of the solvent used (–95° C. in the case of hexane) and preferably between about 5° C. and 35° C. The treatment usually lasts longer than 1 minute, advantageously lasting between about 5 and 60 minutes, and preferably about 15 minutes. This mode of operation can be used with the other organometallic compounds cited hereinabove. The solvent is then removed under vacuum or in inert gas, and the temperature is then increased in order to carry out the grafting operation. The temperature at which the grafting operation is carried out is preferably between about 100° C. and 400° C., and is about 150° C., for example, in the case of $SnBu_4$. For other compounds, and by way of non-limitative example, a temperature is used which is equal to about 250° C. for $GeBu_4$, equal to about 150° C. for $MgNp_2$ and equal to about 80° C. for $ZrNp_4$. The treatment lasts between about 1 hour and 24 hours, preferably about 12 hours.

After grafting, the excess of $SnBu_4$ is removed by one or more rinsing operations with a solvent such as that used hereinabove.

Decomposition of organic fragments

The heat treatment for decomposition of organic fragments is carried out using one of the following methods:

Decomposition of organic fragments in oxidizing atmosphere This treatment is advantageously carried out in the presence of oxygen (preferably a mixture with an inert gas such as nitrogen) at a temperature above 150° C., preferably between 350° C. and 550° C. and about equal to 450° C. This mode of operation for decomposition is worthwhile for all the other grafting agents cited hereinabove.

Decomposition of organic fragments under vacuum

This treatment is advantageously carried out at a temperature of between 350° C. and 550° C., preferably at about 450° C., under dynamic vacuum for four hours. The grafted omega zeolite is then kept at that temperature with an inert gas flow for a period of time of between 10 and 20 hours, preferably for about 15 hours. This mode of operation is suitable for all the other organometallic agents described hereinabove.

The possible depositing of at least one other metal selected from the group IIa, IVb, IIb or IVa metals selected in place of, or in addition to the metal grafted according to the modes of operation given hereinabove is carried out in a similar way.

At the end of the heat treatment for decomposition, the content by weight in the omega zeolite of group IIa, IVb, IIb and/or IVa metals is between 0.01 and 5%, and, advantageously between 0.01 and 4%.

Nonetheless, it is possible to control the level of selectivity of the omega zeolite by carrying out, if necessary, one or more supplementary cycles for "grafting of metal(s) from groups IIa, IVa, IIb or IVb, calcination" in accordance with one of the techniques described hereinabove, in such a way as to obtain contents by weight of metal(s) of said groups (for example magnesium) of between 0.01 and 25%, preferably greater than 5%, and, if necessary, than 7%.

The average and global acid properties of the omega zeolite are not changed by depositing said metal (metals) using the above-described techniques.

Thus, the omega zeolite obtained has a content by weight of sodium in relation to the weight of dry omega zeolite which is less than 2000 ppm, preferably less than 1000 ppm and still more preferably less than 500 ppm, a global Si-Al atomic ratio of between 2.5 and 100, and preferably between 3 and 25.

The properties of the omega zeolite can be measured by the following methods:

the atomic Si/Al ratios are determined by X fluorescence and by nuclear magnetic resonance of silicon 29, the contents of sodium by atomic absorption.

the volume of the elementary mesh and the crystalline structure are determined by X diffraction, the sample of omega zeolite being prepared as in the operatory mode according to the ASTM standard D3942 80 established for faujasite.

The omega zeolite can be subjected (before or after the depositing of at least one metal selected from the group IIa, IVb, IIb and IVa metals) to the depositing of at least one group VIII metal, preferably selected from the group formed by platinum and palladium, and shaped using any technique known to the skilled person. It can, in particular, be mixed with a matrix, usually an amorphous matrix, for example, into a damp powder of alumina gel. The mixture is then shaped by extrusion through a drawplate, for example. The content of omega zeolite of the mixture thus obtained is usually between 0.5 and 99.99% and is advantageously between 40 and 90% by weight in relation to the mixture (omega zeolite+matrix). It is more particularly between about 60 and 85% by weight in relation to the mixture (zeolite+matrix). The content of matrix of the catalyst is usually between about 0.01 and 99.5%, advantageously between about 10 and 60%, and preferably between about 15 and 40% by weight in relation to the mixture (omega zeolite+matrix).

In that which follows, the term, "support" will be used to refer to the mixture of the omega zeolite (on which no metal has been grafted)+matrix.

The shaping operation can be carried out with matrices other than alumina, such as magnesium, silica alumina, natural clays (kaolin, bentonite), for example, and using techniques other than extrusion, such as formation of pastilles or formation of angular figures.

The hydrogenating group VIII metal, preferably Pt and/or Pd, can also be deposited on the support using any process known to the skilled person which enables the metal to be deposited on the omega zeolite. It is possible to use the technique for cationic exchange with competitive agent, preferably ammonium nitrate, the competition ratio being at least equal to about 50 and advantageously about 50 to 200. If platinum or palladium are involved, a tetramine complex of platinum is usually used, or a tetramine complex of palladium; these latter are deposited almost entirely over the omega zeolite. This cationic exchange technique can also be used to deposit the metal directly on the omega zeolite powder before its possible mixture with a matrix.

Depositing of the group VIII metal (or metals) is usually followed by calcination in air or oxygen, usually between 300° and 600° C. for 0.5 to 10 hours, preferably between 350° C. and 550° C. for 1 to 4 hours. It is then possible to reduce it under hydrogen, usually at a temperature of between 300° and 600° C. for 1 to 10 hours; preferably the operation is carried out at between 350° and 550° C. for 2 to 5 hours. The content of group VIII metal (preferably Pt and/or Pd) deposited on the catalyst is obtained at the end of the exchange operation and is usually between 0.05 and 1.5%, preferably between 0.1 and 1%, in weight in relation to the catalyst as a whole.

It is also possible to deposit the platinum and/or palladium not directly on the omega zeolite but on the bonding agent before or after the shaping step, by using an anionic exchange operation with hexachloroplatinic acid, hexachloropalladic acid and/or palladium chloride in the presence of a competition agent such as hydrochloric acid. The catalyst has usually, like before, been subjected to calcination and then reduced with hydrogen, as stated hereinabove, after platinum and/or palladium has/have been deposited.

The bifunctional catalyst obtained using the above operations can be used, in particular, in reactions for the isomerization of an aromatic $C_8$ cut, which may comprise either a mixture of xylenes on its own or a mixture of xylene(s) and ethylbenzene. The isomerization of alkyl-aromatics, particularly xylenes, is of considerable commercial importance. The product is usually paraxylene, in particular, which is the most sought after product because it is used, in particular, as an intermediary in the manufacture of polyester fibers. It is preferable to manufacture paraxylene by isomerization of the metaxylene which can be done by isomerization of orthoxylene. Ethyl benzene which is difficult to separate by distillation from the mixture of xylenes (the boiling points of the various compounds being very similar) is very often found in the isomerization charge of the $C_8$ aromatic hydrocarbons.

The operating conditions of the process for isomerization of a $C_8$ aromatic cut, carried out in the presence of at least one catalyst depending on intervention are usually as follows:

temperature between 270° and 600° C., preferably between 350° and 510° C., pressure between about 0.5 and 100 bars, preferably between 2 and 30 bars, spatial speed (pph) for mass of charge per unit of charge of catalyst and per hour, between 0.5 and 200, preferably between 2 and 100, molar ratio of hydrogen to hydrocarbons of charge ($H_2$/HC) between 0.5 and 12, preferably between 2 and 6.

The following examples illustrate the invention without however limiting its scope; the examples are given for a charge composed of 80% orthoxylene and 20% ethyl benzene (% by weight).

EXAMPLES

Example 1

Catalysts A1 and A2, grafted to tin, and in accordance with the invention.

The raw material used is an omega zeolite which has a global Si/Al atomic ratio of 3.2, a content by weight of sodium in relation to the weight of dry omega zeolite of about 5.3%, a volume of the elemental mesh of 2.196 $nm^3$, and a porous volume in nitrogen measured at −196° C. and with $P/P_o$=0.19 of 0.125 $cm^3$ liquid per gramme.

This omega zeolite is first of all subjected to a calcination treatment, called a dry calcination treatment, at 550° C. in a flow of air and nitrogen for 6 hours. The solid obtained is then subjected to three ionic exchange operations in a solution of $NH_4NO_3$ 1ON at about 100° C. for 4 hours, for each exchange. The omega zeolite is then subjected to a hydrothermal treatment in the presence of 50% water vapor at 625° C. for 4 hours. The zeolite is then subjected to an acid attack with nitric acid 1.5N at about 100° C. for 4 hours in such a way that the species with alumina outside the network which are formed during the hydrothermal treatment are removed. The volume V of the solution of nitric acid used (in ml) is equal to ten times the weight P of dry omega zeolite (V/P=10). The omega zeolite thus has the alumina removed therefrom according to the operatory mode described in the patent EP 214042.

At the end of these treatments, the omega zeolite in H form has a global Si/Al atomic ratio of 11.3, a global Si/Al framework ratio determined by NMR of $^{29}$Si of 12, a content by weight of sodium in relation to the weight of dry omega zeolite of 160 ppm, a volume of the elementary mesh of 2.145 nm$^3$, and an adsorption capacity of nitrogen measured at −196° C. and with P/P$_o$−0.19 of 0.124 cm$^3$ liquid/g.

The tin is then grafted on the outer surface of the crystals of the omega zeolite in H form by the liquid phase method described hereinabove. The organic fragments bonded to the tin after the grafting stage can be decomposed under vacuum or in the presence of air (oxidizing atmosphere).

i) Method of grafting in liquid phase and decomposition of the organic fragments under vacuum.

The following sequence of steps is carried out:

Activation of the omega zeolite by treatment in inert gas at 150° C. for 12 hours, and then reduction of the temperature to 20° C., under inert conditions.

Calcination of possible traces of organic compounds adsorbed into the zeolite with flow of dry air (0.4 l/h/g) and inert gas (2 l/h/g) for 2 hours at 550° C., and then in a flow of dry air only (2 l/h/g) for 2 hours, still at 550° C.

The omega zeolite is cooled to 20° C. in inert gas and is placed in suspension in hexane. The tetrabutyl tin is then injected, still in an atmosphere of inert gas.

After 15 minutes of agitation, the solvent is removed under vacuum. The temperature of the omega zeolite is then increased to 150° C., and is then maintained for 6 hours in an inert atmosphere. After cooling to ambient temperature of the zeolite, the excess of SnBu$_4$ is removed by rinsing with a solution of fresh hexane.

The organic fragments of butyl bonded to the tin are then decomposed by heat treatment under vacuum. To this end, the omega zeolite is placed under dynamic vacuum for 2 hours at a temperature of 450° C., and then in a flow of inert gas for 15 hours. The solid obtained at the end of these treatments is called OM1: its content by weight of tin is 1.3%.

ii) Method of grafting in liquid phase and decomposition of the organic fragments in oxidizing atmosphere The method of obtaining the omega zeolite and the method of grafting it are identical to those described hereinabove which result in the preparation of the solid called OM1. In this example, it is only the method of decomposition of the organic fragments of butyl which are bonded to the tin, it being carried out in an oxidizing atmosphere.

This treatment is carried out in the presence of a mixture of oxygen and inert gas, at 450° C. for 4 hours.

The solid obtained at the end of the treatments is called OM2: its content by weight of tin is 1.26%.

The two solids OM1 and OM2 are then subjected to the same treatments: each is mixed thoroughly with alumina over which 0.3% by weight of platinum is dispersed. The support constituted of the mixture of omega zeolite OM1 and alumina (or omega zeolite OM2 and alumina) contains 39% by weight of alumina. The content by weight of platinum in each of the final A1 catalysts (containing OM1) and A2 catalysts (containing OM2) is thus approximately 0.12%.

The catalysts thus produced are then shaped into pastilles, calcined in air at 500° C. for 2 hours and reduced in hydrogen to 500° C. for 3 hours.

These A1 and A2 catalysts are then tested in an isomerization operation for the orthoxylene mixture (80% by weight) and ethyl benzene (20% by weight) at a temperature of 410° C., at a pressure of 12 bars, at a spatial speed (pph) of 10 (hours)$^{-1}$, and with a molar ratio of hydrogen to hydrocarbons (H$_2$/HC) of about 4.

The performance of the A1 and A2 catalysts (and of the catalysts prepared in the following examples), given in Table 1, are defined by conversion of the o-xylene (%) =

$$\frac{\text{Mass of o-xylene in the charge} - \text{mass of o-xylene in the recipe}}{\text{Mass of o-xylene in the charge}} \times 100$$

Isomerisation selectivity (%) =

$$\frac{\text{Mass m-xylene + mass p-xylene}}{\text{Mass of products}} \times 100$$

Bringing ortho-xylene (AEQ-ox) to equilibrium (%) =

$$\frac{\text{Number of moles of ortho-xylene in recipe}}{\text{Number of moles of ortho-xylene at thermodynamic equilibrium}} \times 100$$

Yield of aromatic C$_8$ (%) =

$$\frac{\text{Mass of C}_8 \text{ aromatic and naphthenes in the recipe}}{\text{Total mass of C}_8 \text{ aromatics in charge}} \times 100$$

Dismutation selectivity (%) =

$$\frac{\text{Mass of trimethyl benzene + mass toluene + mass benzene}}{\text{Mass of products}} \times 100$$

$$\text{Dealkylation selectivity (\%)} = \frac{\text{Mass of benzene}}{\text{Mass of products}} \times 100$$

$$\text{Cracking selectivity (\%)} = \frac{\text{Mass of C1 to C4 gases}}{\text{Mass of products}} \times 100$$

The A1 catalyst, after the catalytic test, is regenerated in accordance with the following mode of operation:

In the presence of a flow of pure nitrogen (3 l/g/h) and at atmospheric pressure the temperature of the catalyst is increased to 150° C. at a rate of 3° C./min. Then, the gaseous mixture of dry air/nitrogen (50/50 by weight) is injected at the location of the nitrogen flow. The temperature is then increased to 550° C. at a rate of 3° C./min. After a level stage of 15 minutes, the gaseous mixture (air/nitrogen) is replaced by a flow of dry air alone (3 l/h/g). A level stage of two hours at the temperature of 550° C. then takes place. The temperature is then reduced to 300° C. with a flow of dry air, and then to ambient temperature with nitrogen.

The catalyst then undergoes a stage of reduction in the presence of hydrogen under the following conditions: with a pressure of hydrogen of 12 bars and with a pph equal to 5 with hydrogen, the catalyst is heated at a rate of 3° C./min to 150° C., with a level stage of 2 hours taking place at this temperature. The same operation is carried out at temperatures of 250° C., 350° C. and 450° C., the speed at which the temperature increases between each level stage being 3° C./min. The catalyst is then cooled with hydrogen until ambient temperature is reached.

The regenerated A1R catalyst thus obtained is once again tested during isomerization of the mixture of ortho-xylene (80% by weight) and ethyl benzene (20% by weight) at a temperature of 410° C. at a pressure of 12 bars with a spatial speed (pph) of 50 (hour)$^{-1}$ and a molar ratio of hydrogen to hydrocarbons (H$_2$/HC) of about 4. The performances of the A1R catalyst are shown in Table II.

Example 2

Catalyst A3 grafted to tin, in accordance with the invention.

The raw material used is the same omega zeolite as that used in Example 1. It has a global Si/Al atomic ratio of 3.2, a content by weight of sodium in relation to the weight of dry omega zeolite of about 5.3%, a volume of the elemental mesh of 2.196 nm$^3$ and a porous volume with nitrogen measured at −196° C. and with $P/P_o$ 0.19 of 0.125 cm$^3$ liquid per gramme.

Nonetheless, in this example the omega zeolite does not have the alumina removed therefrom. It is subjected during a first stage to a calcination operation known as a dry calcination operation at 550° C. with a flow of air and nitrogen for 6 hours. The solid obtained is then subjected to three ionic exchanges in a 10N solution of $NH_4NO_3$ at about 100° C. for 4 hours for each exchange. The ammonium form of the omega zeolite thus obtained is then calcined during a first stage with a flow of dry air diluted in nitrogen (0.4 l/h/g dry air for 2 l/h/g nitrogen) for 2 hours, and then with a flow of dry air alone for 4 hours at a temperature of 550° C.

At the end of these treatments, the omega zeolite in H form thus obtained has a global Si/Al atomic ratio of 3.25, a global framework Si/Al ratio, calculated by NMR of $^{29}$Si of 3.2, a content by weight of sodium in relation to weight of dry omega zeolite of 150 ppm, a volume of the elemental mesh of 2,207 nm$^3$, and an adsorption capacity of nitrogen as measured at −196° C. and with $P/P_o$=0.19 of 0.22 cm$^3$ liquid/g.

The method of grafting the omega zeolite in H form with a global Si/Al ratio of 3.2 which has been obtained previously is carried out using the gaseous phase method in accordance with the following sequence of steps:

Activation of the omega zeolite by treating it in inert gas at 150° C. for 12 hours, and then reducing the temperature to 20° C. in inert gas.

Calcination of possible traces of organic compounds adsorbed in the zeolite in a flow of dry air (0.4 l/h/g) and inert gas (2 l/h/g)) for 2 hours at 550° C., and then in a flow of dry air alone (2 l/h/g) for 2 hours still at 550° C.

The zeolite is then cooled in a dynamic vacuum until ambient temperature is reached, and is placed in a static vacuum (10$^{-4}$ Torr). Tetrabutyl tin is then injected at 25° C. by the intermediary of a septum.

The temperature of the reaction medium is then increased to 150° C., and is then kept at this temperature for 6 hours. After grafting, the excess of SnBu$_4$ present in the system is removed by purging under dynamic vacuum or in inert gas.

The method for decomposition of the organic fragments (butyls) is identical to that used in obtaining the solid called OM2 in Example 1.

The solid obtained after these treatments is called OM3: its content by weight of tin is 1.2%, its other characteristics remain unchanged from those for the omega zeolite in H form.

The steps of mixing the omega zeolite and alumina and of dispersing the platinum, of shaping and reducing the catalyst, and the isomerisation test conditions are identical to those described in Example 1.

The performance of the A3 catalyst thus obtained (the content by weight of platinum of which is about 0.12%) are given in Table 1.

The A3 catalyst, after the catalytic test, is regenerated according to the mode of operation described in Example 1, and is tested again under the conditions described in Example 1. The performance of the A3R catalyst thus regenerated are given in Table II.

Example 3

A4 catalyst grafted on germanium, in accordance with the invention.

The omega zeolite in H form with a global Si/Al ratio of 11.3 which is used in the preparation of the OM4 catalyst is the same as that used in the preparation of the OM1 and OM2 catalysts in Example 1.

The germanium is then deposited on the outer surface of the crystals of said omega zeolite in H form in accordance with the gaseous phase method. The operation is carried out in accordance with the following sequence of steps:

Activation of the zeolite under dynamic vacuum, at a temperature of 160° C., for 8 hours. The temperature is then increased at a speed of 2° C. /min to 450° C., and is kept under dynamic vacuum for 9 hours. The temperature is then lowered to 250° C., this being the temperature at which the GeBu$_4$ is injected. The omega zeolite is then left under a tension of GeBu$_4$ vapour for 48 hours at 250° C. After returning to ambient temperature (20° C.), the released gases are removed under dynamic vacuum, and the residual physisorbed species are desorbed under dynamic vacuum for 8 hours at 220° C. The butyl fragments which are fixed to the germanium are then decomposed by heat treatment in an oxidizing atmosphere. This treatment is carried out in the presence of a mixture of oxygen and inert gas at 450° C. for 4 hours.

The solid obtained after these treatments is called OM4: its content by weight of germanium is 0.31%, its other characteristics remain unchanged from those of the omega zeolite in H form.

The steps of mixing the omega zeolite and alumina, of dispersing the platinum, of shaping and reducing the catalyst, and the conditions of the isomerisation test are identical to those described in Example 1.

The performance of the A4 catalyst thus obtained (the content by weight of platinum of which is about 0.12%) are given in Table 1.

Example 4

A5 Catalyst, grafted to zirconium, in accordance with the invention.

The omega zeolite, in H form, which is used in the preparation of the OM5 solid is the same as that used in the preparation of the OM1, OM2 solids in Example 1 and of OM4 in Example 3.

Zirconium is then deposited on the outer surface of the crystals of said omega zeolite in H form in accordance with the gaseous phase method. The operation is carried out in accordance with the following sequence of steps:

Activation of the zeolite in dynamic vacuum of the zeolite, at a temperature of 160° C., for 8 hours. The temperature is then increased at a speed of 2° C./min until 450° C. is reached, and it is kept under dynamic vacuum for 14 hours.

Sublimation of ZrNp4 at 70° C. under dynamic vacuum.—Treatment at 60° C. under dynamic vacuum for one hour, in order to remove all of ZrNp4.

Placing under tension of water vapor at 25° C. (about 23 mmHg) in order to transform the alkyl moieties into hydroxyl groups.—Treatment at 250° C. under dynamic vacuum for 14 hours in order to remove residual water. A heat treatment in an oxidising atmosphere is carried out in the presence of a mixture of oxygen and inert gas at 450° C. for 4 hours.

The solid obtained at the end of these treatments is called OM content by weight of zirconium is 0.42%, its other characteristics remain unchanged from those of the omega zeolite in H form.

The steps for mixing the omega zeolite and alumina, for dispersing the platinum, for shaping and reducing the catalyst, and the conditions of the isomerization test are identical to those described in Example 1.

The performances of the A5 catalyst thus obtained (the content by weight of platinum of which is about 0.12%) are given in Table 1.

Example 5

A6 Catalyst, not in accordance with the invention.

The A6 catalyst contains omega zeolite in H form with a global Si/Al ratio of 11.3 used in the preparation of the catalyst A1, A2, A4 and A5. However, no grafting operation is carried out.

The steps for mixing the omega zeolite and alumina, for dispersing the platinum, for shaping and reducing the catalyst, and the conditions of the isomerization test are identical to those described in Example 1.

The performances of the A6 catalyst thus obtained (the content by weight of platinum of which is about 0.12%) are given in Table 1.

The A6 catalyst, after the catalytic test, is regenerated in accordance with the mode of operation described in Example 1, and is tested once again under the conditions described in Example 1. The performance of the catalyst A6R thus regenerated are given in Table II.

Example 6

Catalyst A7, not in accordance with the invention.

The catalyst A7 contains omega zeolite in H form, with a global Si/Al ratio of 3.25, used in the preparation of the A3 catalyst. However, no grafting operation is carried out.

The steps for mixing the omega zeolite and alumina, for dispersing the platinum, for shaping and reducing the catalyst, and the conditions of the isomerisation test are identical to those described in Example 1.

The performances of the A7 catalyst thus obtained (the content by weight of platinum of which is about 12%) are given in Table 1.

The A7 catalyst, after the catalytic test, is regenerated in accordance with the mode of operation described in Example 1, and is tested once again under the conditions described in Example 1. The performances of the A7R catalyst thus regenerated are given in Table II.

Example 7

A8 Catalyst, not in accordance with the invention.

The A8 catalyst contains a mordenite in H form, with a global Si/Al ratio of 11. SnBu4 is grafted to the outer surface of the crystals of the mordenite in H form, in accordance with the liquid phase method, identical to that used in the preparation of the A1 catalyst in Example 1.

Likewise, the method of decomposition under vacuum of the butyl groups bonded to the tin is the same as that used during the preparation of the A1 catalyst in Example 1. The solid obtained at the end of these treatments is called OM1, and its content by weight of tin is 1.34%.

The steps of mixing the omega zeolite and alumina, of dispersing the platinum, of shaping and reducing the catalyst and the conditions of the isomerisation test are identical to those described in Example 1.

The performances of the A8 catalyst thus obtained (the content by weight of platinum of which is about 0.12%) are given in Table 1. After the catalytic test, the catalyst A8 is regenerated in accordance with the mode of operation described in Example 1. The performances of the catalyst A8R are given in Table II.

Effect of Grafting on the iso-approach selectivities at equilibrium

Table 1 describes the performances of the catalysts A1, A2, A3, A4, A5, A6 and A7, compared with iso approach at equilibrium, not regenerated and prepared in accordance with the modes of operation described hereinabove. The effect of grafting on the selectivities is particularly evident.

The catalysts A1, A2, A3, A4, A5, A6 and A7 have been tested under the conditions described hereinabove, namely isomerisation of a mixture of orthoxylene (80% by weight) and ethyl benzene (20% by weight), at a temperature of 410° C. at a pressure of 12 bars, at a spatial speed (pph) of 10 (hour)$^{-1}$ and with a molar ratio of hydrogen to hydrocarbons ($H_2$/HC) of about 4.

TABLE 1

Effect of Grafting on iso-approach selectivities at equilibrium

| Catalyst | A1 | A2 | A3 | A4 | A5 | A6 | A7 | A8 |
|---|---|---|---|---|---|---|---|---|
| Example | 1 | 1 | 2 | 3 | 4 | 5 | 6 | 7 |
| pph (h$^{-1}$) | 10 | 10 | 10 | 10 | 10 | 10 | 10 | 14 |
| (%) AEQ o-xylene | 90.3 | 91.1 | 90.6 | 91.0 | 90.8 | 90.5 | 91.0 | 91.3 |
| Yield of $C_8$ Aromatics + Naphthenes % | 93.8 | 94.1 | 94.3 | 93.7 | 94.6 | 88.2 | 90.5 | 90.2 |
| % Dismutation | 2.9 | 2.8 | 2.1 | 3.0 | 2.1 | 8.3 | 6.1 | 6.5 |
| % Dealkylation | 0.8 | 0.7 | 0.5 | 0.9 | 0.6 | 1.5 | 1.3 | 1.7 |
| % Cracking | 2.1 | 2.2 | 2.0 | 1.7 | 1.4 | 1.9 | 1.8 | 1.6 |

The catalysts A1, A2, A3, A4 and A5 in accordance with the invention have a higher performance than the catalysts A6 and A7 of the prior art: the yield during isomerization of $C_8$ aromatics + naphthenes of the catalysts A1, A2, A3, A4 and A5 is greater than that of the catalysts A6 and A7. With the omega zeolites selected according to the invention (catalysts A1, A2, A3, A4 and A5), the secondary dismutation reaction resulting in the formation of trimethyl benzenes is very greatly inhibited in comparison with that obtained in the presence of non selected omega zeolite (catalyst A6 and A7). On the other hand, it is noted that a reduction in the global Si/Al ratio of the zeolite also causes a reduction in the rate of dismutation, both in the case of non-grafted zeolite (catalyst A7) and also in the case of grafted zeolite (catalyst A3). The A8 catalyst not in accordance with the invention (grafted mordenite) does not lead to a as low a dismutation rate as that recorded in the case of the catalysts with a base of grafted omega zeolite. The results obtained during isomerization of the aromatic $C_8$ cut are thus far better than those obtained with grafted mordenite and are quite unexpected.

Results almost the same as those recorded with the catalysts A1, A2, A3, A4 and A5 are obtained by replacing tin first of all with magnesium and then with titanium and finally with zinc.

Effect of the regeneration treatments

Table II describes the performance of the catalysts A1R, A6R and A7R which contain omega zeolite and which are regenerated in accordance with the modes of operation described in Example 1, and of the catalyst A8R which is regenerated and which contains mordenite. These catalysts have been prepared in accordance with the modes of operation described hereinabove. The effect of the regeneration treatment on catalytic activity and on the selectivities is particularly evident.

The catalysts A1R, A3R, A6R, A7R and A8R have been tested under the conditions described hereinabove, namely isomerization of a mixture of orthoxylene (80% by weight) and ethyl benzene (20% by weight), at a temperature of 410° C., at a pressure of 12 bars, at a spatial speed (pph) of 50 (hour)$^{-1}$ and with a molar ratio of hydrogen to hydrocarbons ($H_2$/HC) of about 4.

TABLE II

Effect of Iso-Approach Regeneration Treatments at equilibrium

| Catalyst | A1R | A3R | A6R | A7R | A8R |
|---|---|---|---|---|---|
| Example | 1 | 2 | 5 | 6 | 7 |
| pph (h$^{-1}$) | 50 | 50 | 50 | 50 | 14 |
| AEQ o-xylene | 90.9 | 90.5 | 91.0 | 90.7 | 91.0 |
| Yield of C$_8$ aromatics + naphthenes % | 94.0 | 94.4 | 88.4 | 90.6 | 90.2 |
| % Dismutation | 2.6 | 1.9 | 8.2 | 6.0 | 6.6 |
| % Dealkylation | 0.7 | 0.9 | 0.4 | 0.8 | 1.8 |
| % Cracking | 2.0 | 1.9 | 2.1 | 1.8 | 1.5 |

The results in Table II show that surprisingly the regeneration treatments carried out on the catalysts with a base of omega zeolites grafted on tin (A1R and A3R) are much more active than the non-regenerated catalysts (A1 and A3). In fact, in the case of catalysts with a base of omega zeolite which are not regenerated, a pph of 10 h$^{-1}$ results in an approach at equilibrium of ortho-xylene in the order of 90%, this value being obtained by imposing a pph of 50 h$^{-1}$ in the case of the regenerated A1R and A3R catalysts. Activity is therefore multiplied by a factor of 5. Moreover, it is also noted surprisingly that the rates of dismutation recorded in the case of catalysts with a base of omega zeolites grafted on tin (A1R and A3R) are lower than those obtained in the case of non-regenerated catalysts. Such effects, caused by the regeneration treatments, are not observed in the case of the A8R catalyst with a base of non-grafted omega zeolite, and in the case of the A8R catalyst with a base of mordenite grafted via SnBu$_4$. In fact, for the regenerated A8R catalyst it is noted that it is necessary to keep a pph of 14 (h$^-$) in order to obtain catalytic performance comparable to those obtained with the non-regenerated A8 catalyst, which is also tested with a pph of 14.

Similar effects on catalytic activity and the rate of dismutation after the regeneration treatments have been observed in the case of catalysts with a base of omega zeolite grafted to germanium and zirconium.

We claim:

1. A process for isomerisation of a C$_8$ aromatic cut at a temperature of between 270° C. and 600° C., a pressure of 0.5 to 100 bars, a spatial speed of charge per unit of charge of catalyst and per hour of between 0.5 and 200 and a H$_2$/hydrocarbon molar ratio of between 0.5 and 12, in which process a catalyst is used which has an omega zeolite base and which contains a matrix, at least one group VIII metal and an omega zeolite containing at least one metal selected from group IIa, IIb, IVa and IVb metals and such that:

its global Si/Al atomic ratio is between 1.5 and 100, its content by weight of sodium in relation to the weight of dry omega zellite is less than 2000 ppm, the metal(s) is/are deposited on the omega zeolite by grafting with at least one organometallic compound of said metal(s).

2. A process according to claim 1, wherein the matrix is alumina, magnesia, silica-alumina or a natural clay, and the grafted metal is tin magnesium, germanium or zirconium.

3. A process according to claim 2, wherein the catalyst is regenerated after having been placed in contact with the charge under isomerisation conditions of the aromatic C$_8$ cut.

4. A process according to claim 1, wherein the catalyst is obtained by the process comprising depositing by grafting on the omega zeolite at least one of the group IIa, IVb, IIb, and IVa metals, and then mixing the grafted omega zeolite with a matrix containing a group VIII metal.

5. A process according to claim 1, wherein the catalyst is obtained by the process comprising depositing by grafting on the omega zeolite at least one of the group IIa, IVb, IIb, and IVa metals, and then mixing the grafted omega zeolite with a matrix and depositing the group VIII metal.

6. A process according to claim 1, wherein the catalyst is obtained by the process comprising depositing by grafting on the omega zeolite at least one of the group IIa, IVb, IIb, and IVa metals, said depositing being preceded by, or followed by, the depositing of at least one group VIII metal, the grafted zeolite which is charged with the group VIII metal then being mixed with the matrix.

7. A process according to claim 1, wherein the grafting operation takes place in liquid phase, the organometallic compound being in solution in a solvent, said solvent being an alkane with at least 5 carbon atoms.

8. A process according to claim 1, wherein the grafted metal is selected from the group formed by tin, magnesium, germanium and zirconium.

9. A process according to claim 1, wherein the content by weight of group IIa, IIb, IVa, IVb metals of said omega zeolites between 0.01 and 25%.

10. A process according to claim 1, wherein the group VIII metal is selected from the group formed by palladium and platinum.

11. A process according to claim 1, wherein the matrix is selected from the group formed by alumina, magnesium, silica-alumina, and natural clays.

* * * * *